(12) United States Patent
Aoyagi et al.

(10) Patent No.: US 9,700,274 B2
(45) Date of Patent: Jul. 11, 2017

(54) IMAGE OBSERVATION APPARATUS AND STORAGE MEDIUM THAT GENERATES A PLURALITY OF IMAGE LISTS

(71) Applicant: Toshiba Medical Systems Corporation, Otawara-shi (JP)

(72) Inventors: Kota Aoyagi, Nasushiobara (JP); Satoshi Wakai, Nasushiobara (JP); Kazumasa Arakita, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/731,859

(22) Filed: Jun. 5, 2015

(65) Prior Publication Data
US 2015/0265233 A1    Sep. 24, 2015

Related U.S. Application Data

(63) Continuation of application No. PCT/JP2013/082734, filed on Dec. 5, 2013.

(30) Foreign Application Priority Data

Dec. 5, 2012   (JP) ................................ 2012-266444
Dec. 5, 2013   (JP) ................................ 2013-251907

(51) Int. Cl.
*A61B 6/00*        (2006.01)
*G06F 17/30*       (2006.01)
(Continued)

(52) U.S. Cl.
CPC .............. *A61B 6/463* (2013.01); *A61B 5/002* (2013.01); *A61B 5/0035* (2013.01); *A61B 5/743* (2013.01);
(Continued)

(58) Field of Classification Search
None
See application file for complete search history.

(56) References Cited

U.S. PATENT DOCUMENTS 6,976,231 B1 * 12/2005 Funahashi ........... G06F 3/04845
                                                 715/853
2012/0278359 A1 * 11/2012 Igarashi ................ G06F 19/321
                                                 707/769

FOREIGN PATENT DOCUMENTS

JP      2001-134685 A    5/2001
JP      2008-192044 A    8/2008
(Continued)

OTHER PUBLICATIONS

U.S. Appl. No. 14/729,246, filed Jun. 3, 2015, Arakita et al.
(Continued)

*Primary Examiner* — Maurice L McDowell, Jr.
(74) *Attorney, Agent, or Firm* — Oblon, McClelland, Maier & Neustadt, L.L.P.

(57) ABSTRACT

According to one embodiment, an image observation apparatus includes a condition storage, list generation circuitry, and a display. The condition storage stores a plurality of display target conditions respectively corresponding to a plurality of display areas in a display screen. The list generation circuitry generates a plurality of image lists respectively corresponding to the plurality of display areas, which concern additional items of a plurality of images respectively corresponding to the display target conditions. The display displays the plurality of image lists in the plurality of display areas, and an image corresponding to an additional item selected from the plurality of displayed image lists in the corresponding display area.

11 Claims, 8 Drawing Sheets

(51) Int. Cl.
*A61B 5/00* (2006.01)
*G06F 3/14* (2006.01)
*G09G 5/14* (2006.01)

(52) U.S. Cl.
CPC .......... *A61B 5/7425* (2013.01); *A61B 5/7435* (2013.01); *A61B 6/5294* (2013.01); *A61B 6/563* (2013.01); *G06F 3/1446* (2013.01); *G06F 17/30277* (2013.01); *G09G 5/14* (2013.01); *G09G 2380/08* (2013.01)

(56) References Cited

FOREIGN PATENT DOCUMENTS

| JP | 2010-82002 A | 4/2010 |
|----|--------------|--------|
| JP | 2011-24688 A | 2/2011 |
| JP | 2012-157688 A | 8/2012 |
| JP | 2013-114485 A | 6/2013 |

OTHER PUBLICATIONS

International Search Report issued Jan. 21, 2014 for PCT/JP2013/082734 filed on Dec. 5, 2013 with English Translation.
Written Opinion issued Jan. 21, 2014 for PCT/JP2013/082734 filed on Dec. 5, 2013.

* cited by examiner

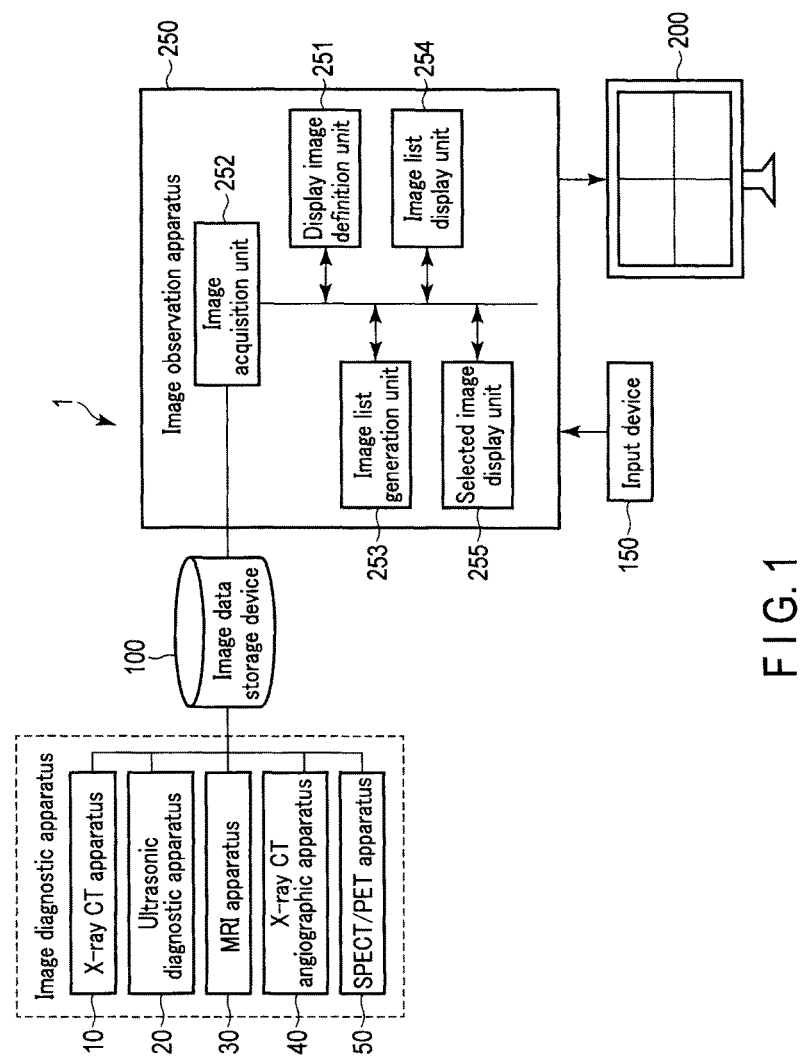
F I G. 1

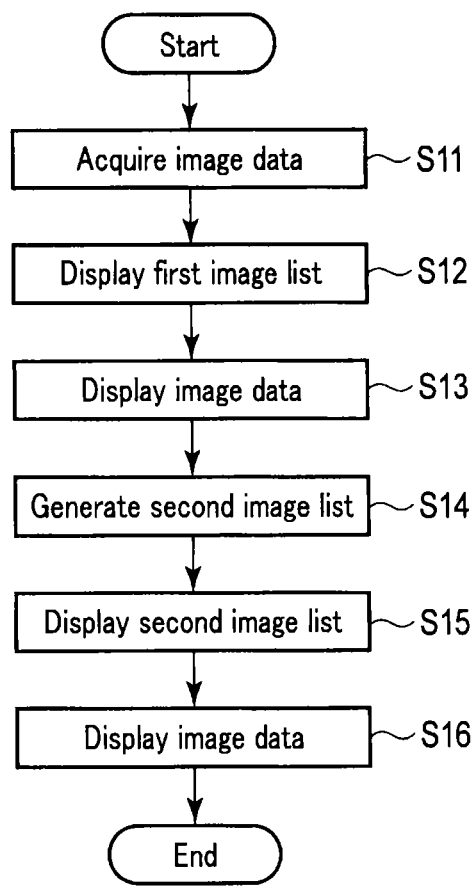
F I G. 8

IMAGE OBSERVATION APPARATUS AND STORAGE MEDIUM THAT GENERATES A PLURALITY OF IMAGE LISTS

CROSS-REFERENCE TO RELATED APPLICATIONS

This application is a Continuation Application of PCT Application No. PCT/JP2013/082734, filed Dec. 5, 2013 and based upon and claims the benefit of priority from the Japanese Patent Application No. 2012-266444, filed Dec. 5, 2012; and No. 2013-251907, filed Dec. 5, 2013, the entire contents of all of which are incorporated herein by reference.

FIELD

Embodiments described herein relate generally to an image observation apparatus and a storage medium.

BACKGROUND

In medical image diagnosis, various image diagnostic apparatuses (to be also referred to as modalities hereinafter) are used, including an X-ray CT (Computed Tomography) apparatus, ultrasonic diagnostic apparatus, MRI (Magnetic Resonance Imaging) apparatus, X-ray CT angiographic apparatus, and SPECT/PET apparatus in accordance with diagnostic purposes.

In general, a plurality of types of image data captured by a plurality of modalities (to be also referred to as multimodalities hereinafter) are transmitted to, for example, an image observation apparatus in a PACS (Picture Archiving and Communication System). The image observation apparatus incorporates in advance an image viewer for displaying image data. Upon receiving image data, the image observation apparatus displays the received imaged data on a screen of a monitor. In this case, the image observation apparatus is preferably capable of simultaneously displaying a plurality of types of image data on a screen to allow the operator to comprehensively observe a morphological image and a functional image or comparatively observe a past study image and a current study image.

For this reason, there is recently available an image observation apparatus incorporating an image viewer having a multimodality function capable of simultaneously displaying a plurality of types of image data on a screen. This image observation apparatus divides an image display area on the monitor capable of displaying image data into a plurality of areas and displays a plurality of types of image data in the respective areas. The operator can arbitrarily select image data to be displayed in each area while referring to an image list. In this case, the image list is a list of all image data received by the image observation apparatus. This list is displayed on a screen when the operator selects image data to be displayed in each area.

According to the above image observation apparatus, however, since an image list is a list of all image data received by the image observation apparatus, it takes time for the operator to select desired image data from the image list, resulting in inefficiency.

BRIEF DESCRIPTION OF DRAWINGS

FIG. 1 is a schematic view showing an example of the arrangement of a medical image display system including an image observation apparatus according to the first embodiment.

FIG. 8 is a flowchart showing an example of the operation of the image observation apparatus according to this embodiment.

DETAILED DESCRIPTION

In general, according to one embodiment, an image observation apparatus includes a condition storage, list generation circuitry, and a display. The condition storage configured to store a plurality of display target conditions respectively corresponding to a plurality of display areas in a display screen. The list generation circuitry configured to generate a plurality of image lists respectively corresponding to the plurality of display areas, which concern additional items of a plurality of images respectively corresponding to the display target conditions. The display configured to display the plurality of image lists in the plurality of display areas, and an image corresponding to an additional item selected from the plurality of displayed image lists in the corresponding display area.

An image observation apparatus and its storage medium according to each embodiment will be described below with reference to the accompanying drawings. The following image observation apparatus can be implemented by a hardware arrangement or a composite arrangement of hardware resources and software. The software of the composite arrangement to be used includes programs which are preinstalled from a network or storage medium into a computer to cause the computer to implement each function of the image observation apparatus or a storage medium storing the programs.

[First Embodiment]

Figure 2:
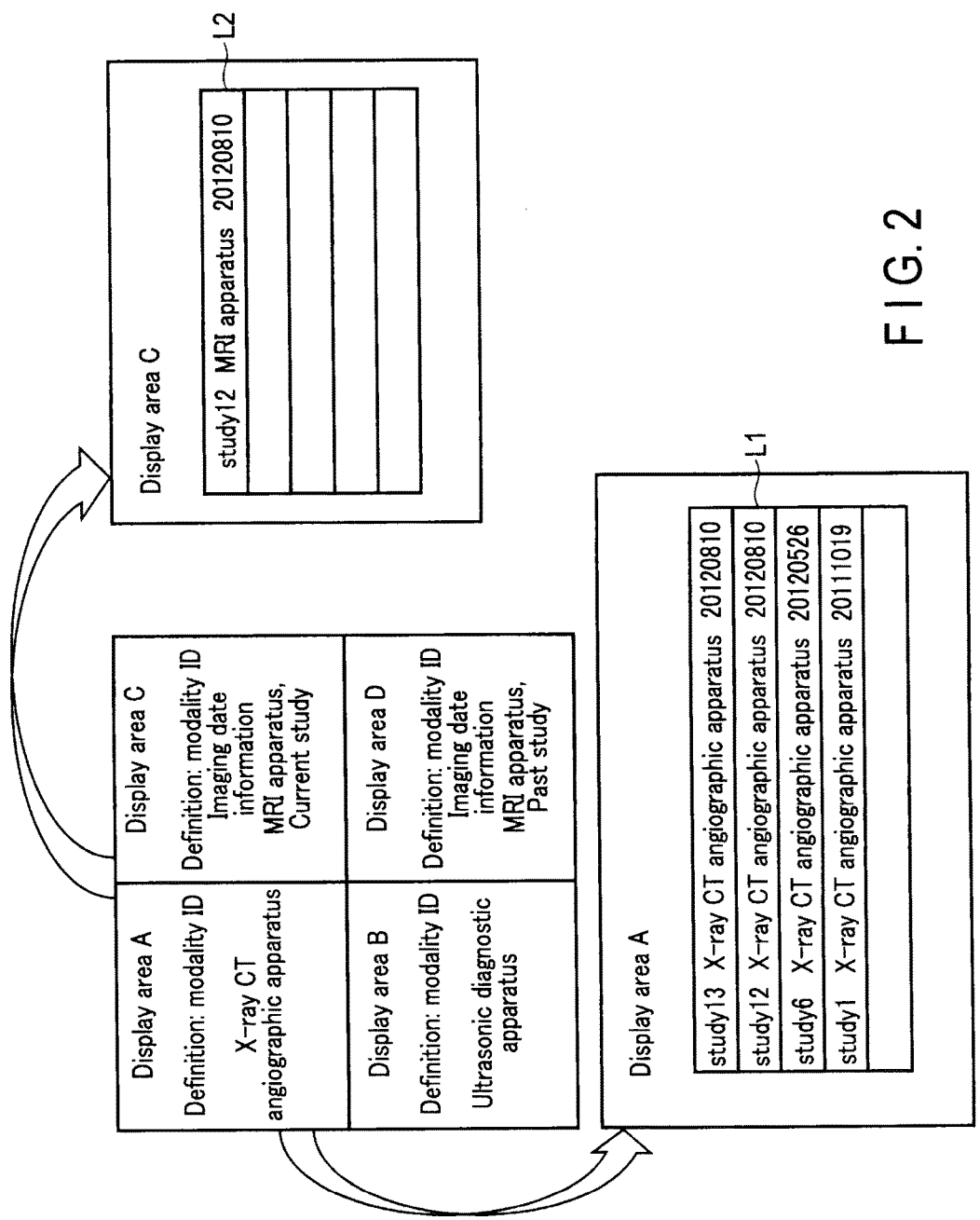
FIG. 2 is a schematic view showing an example of the image list generated by the image observation apparatus according to this embodiment.
Figure 3:
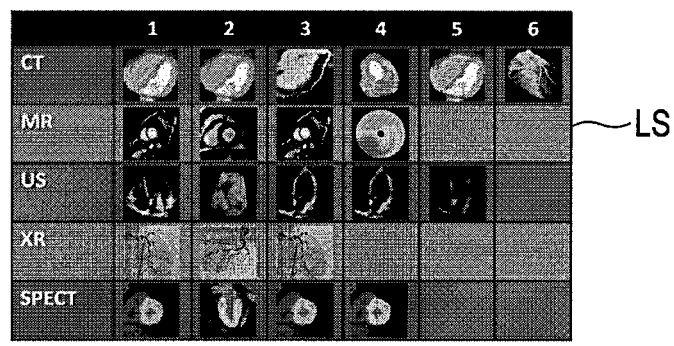
FIG. 3 is a schematic view showing an example of the image list generated by the image observation apparatus according to this embodiment.
Figure 4:
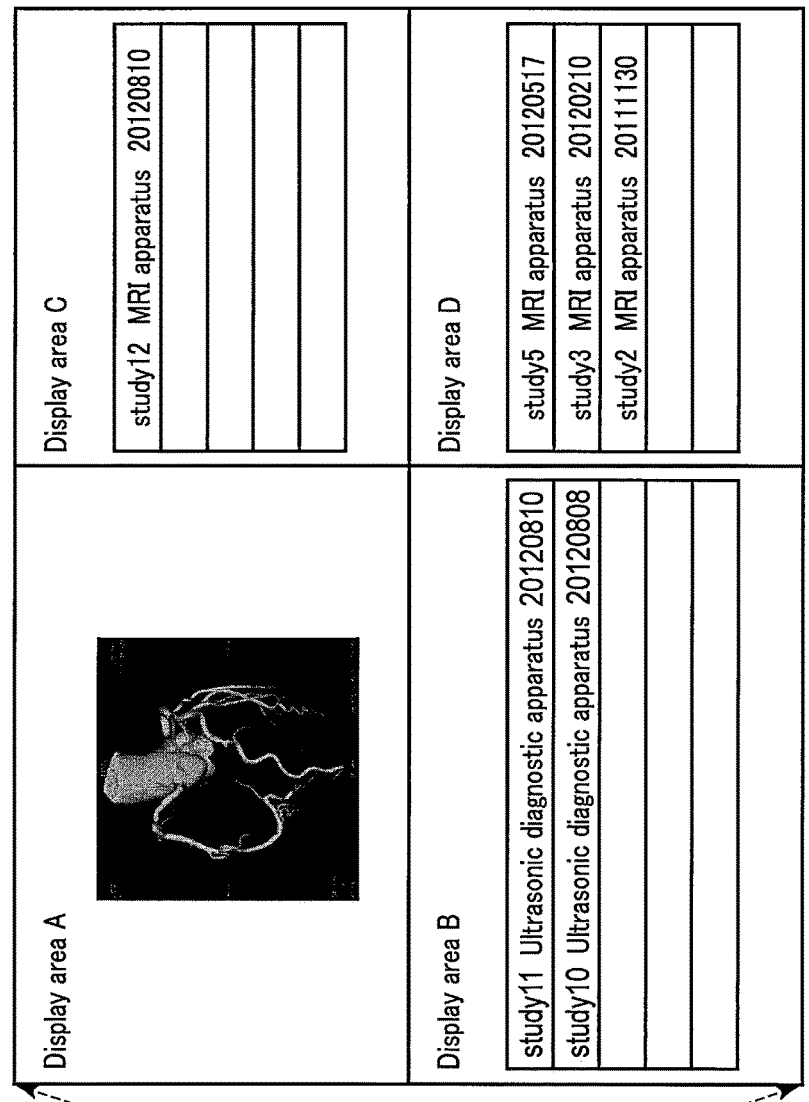
FIG. 4 is a schematic view showing an example of a screen displayed on a monitor by the image observation apparatus according to this embodiment.

FIG. 1 is a schematic view showing an example of the arrangement of a medical image display system including an image observation apparatus according to the first embodiment. FIGS. 2 and 3 are schematic views showing an example of the image list generated by the image observation apparatus according to this embodiment. FIG. 4 is a schematic view showing an example of the screen displayed on a monitor by the image observation apparatus according to the embodiment. A medical image display system 1 shown in FIG. 1 includes a plurality of image diagnostic apparatuses 10, 20, . . . , 50, an image data storage device 100, an input device 150, a monitor 200, and an image observation apparatus 250. Note that the image diagnostic apparatuses 10, 20, 30, 40, and 50 are communicatively connected to the image data storage device 100, and the image data storage device 100 is communicatively connected to the image observation apparatus 250. The functions of the apparatuses 10, 20, 30, 40, 50, 100, 150, 200, and 250 will be described in detail below.

The image diagnostic apparatuses 10, 20, 30, 40, and 50 are apparatuses which can capture medical images. For example, as shown in FIG. 1, they include the X-ray CT apparatus 10, the ultrasonic diagnostic apparatus 20, the MRI apparatus 30, the X-ray CT angiographic apparatus 40, and the SPECT/PET apparatus 50. Note that although this embodiment has exemplified the X-ray CT apparatus 10, the ultrasonic diagnostic apparatus 20, the MRI apparatus 30, the X-ray CT angiographic apparatus 40, and the SPECT/PET apparatus 50 as typical image diagnostic apparatuses, the embodiment is not limited to them, and any apparatuses which can capture medical images can be used as image diagnostic apparatuses constituting the medical image display system 1, as needed.

The image data storage device 100 is a storage device which stores a plurality of types of image data captured by the image diagnostic apparatuses 10, 20, 30, 40, and 50. Each image data is a so-called DICOM (Digital Imaging Communications and Medicine) image file complying with standard specifications in the image study field, and has additional information. Additional information includes a plurality of additional items. Additional information always includes an additional item concerning a patient ID for identifying a patient. Furthermore, in addition to a patient ID, each additional item includes at least one of the following: a modality ID for identifying each of the image diagnostic apparatuses 10, 20, 30, 40, and 50, imaging date information indicating an imaging date, imaging region information indicating an imaging region, type information indicating whether the corresponding image data is a morphological image or functional image, image acquisition conditions (a scan condition and imaging conditions), contrast agent information (the type of contrast agent, injection amount, injection time, and the like), an study order (a study region, study purpose, and the like), study ID, and series ID.

Note that the image data storage device 100 functions not only as a storage medium which stores the image data captured by the image diagnostic apparatuses 10, 20, 30, 40, and 50 but also as a server apparatus including a communication unit (not shown) which can communicate with the image diagnostic apparatuses 10, 20, 30, 40, and 50 and the image observation apparatus 250. In addition, in this embodiment, additional information contains various types of additional items described above. However, the embodiment is not limited to this. For example, additional information may further contain an image ID assigned to each image data.

The input device 150 is an input interface which executes various types of input processing for the image observation apparatus 250 in accordance with an operation by the operator, and includes, for example, a mouse, keyboard, and touch panel. Various types of input processing include input processing for a patient ID and input processing for definition information (to be described later) and a list display request.

The monitor 200 is a display apparatus which displays the image data acquired by the image observation apparatus 250. Note that the monitor 200 has a function of dividing one display area into a plurality of display areas to display a plurality of image data on the same screen. The operator can arbitrarily set the number of display areas via the input device 150.

In this case, as shown in FIG. 1, the image observation apparatus 250 includes a display image definition unit 251, an image acquisition unit 252, an image list generation unit 253, an image list display unit 254, and a selected image display unit 255. The functions of the units 251 to 255 constituting the image observation apparatus 250 will be described in detail below.

The display image definition unit 251 defines display target conditions which are conditions for deciding image data as display targets in a plurality of display areas on the monitor 200 in accordance with an operation by the operator, and which contain at least one additional item (excluding a patient ID) in additional information. More specifically, upon accepting the input of the definition information input from the input device 150, the display image definition unit 251 defines a display target condition by writing the accepted input of the definition information in a memory (not shown). In this case, definition information is the information in which an area ID for identifying a display area is associated with display target condition information indicating an additional item to be contained in the additional information added to image data as a display target in the display area. The definition information is also information to which the image list generation unit 253 can refer as needed. Note that as described above, display target condition information in definition information may contain at least one of a modality ID, imaging date information, imaging region information, and type information. However, for example, these pieces of information may be combined as needed (for example, a modality ID and imaging date information) or may contain a plurality of pieces of information of the same type with different values (for example, a plurality of modality IDs with different values).

FIG. 2 schematically shows that display target conditions for deciding image data as display targets in the respective display areas are defined for the respective display areas. FIG. 2 also indicates that image data containing the modality ID of an X-ray CT angiographic apparatus in additional information is a display target in a display area A. That is, the memory (not shown) stores the definition information in which an area ID for specifying the display area A is associated with a modality ID for specifying an X-ray CT angiographic apparatus as display target condition information. FIG. 2 also indicates that image data containing the modality ID of an MRI apparatus and the imaging date information of the current study in additional information is a display target in a display area C. That is, the memory (not shown) stores definition information in which an area ID for specifying the display area C is associated with a modality ID for specifying an MRI apparatus and imaging date information indicating the current study as display target condition information. The display image definition unit 251 can differentiate definition information to be used for each display area in this manner.

Note that this embodiment has defined display target conditions for deciding image data as display targets in the respective display areas by storing the definition information input from the input device 150 in the memory (not shown). However, a method of defining display target conditions is not limited to this. For example, the definition method described below may be used. However, assume that in this case, the memory (not shown) stores in advance diagnosis scene information in which a diagnosis scene is associated with display target condition information representing information to be contained in the additional information of image data generally used in the diagnosis scene. In this case, upon accepting the input of the diagnosis scene input from the input device 150, the display image definition unit 251 extracts the display target condition information associated with the accepted input diagnosis scene while referring to the diagnosis scene information stored in the memory (not shown). The display image definition unit 251 then defines display target conditions for deciding image data as a display target in each display area by writing the extracted display target condition information as definition information in the memory (not shown). Note that a diagnosis scene is a "diagnosis before an operation for angina pectoris as a cardiovascular disease" or the like. This allows the operator to more intuitively define display target conditions.

Upon accepting the input of the patient ID input from the input device 150, the image acquisition unit 252 acquires image data containing the accepted input patient ID in additional information from the image data storage device 100.

The image list generation unit 253 narrows down the image data from the image acquisition unit 252 based on the display target conditions defined by the display image definition unit 251, and generates an image list concerning some (additional items) of the pieces of additional information of the narrowed-down image data for each display area.

List generation processing by the image list generation unit 253 will be described in detail below. First of all, the image list generation unit 253 accepts the input of the list display request input from the input device 150. In this case, a list display request is a request to designate one of the display areas on the monitor 200, and is a request to display an image list concerning the additional items of image data as a display target in the display area. Subsequently, the image list generation unit 253 narrows down the image data acquired by the image acquisition unit 252 to only image data satisfying the display target conditions defined in the display area designated by the list display request while referring to the definition information stored in the memory (not shown). The image list generation unit 253 then generates an image list concerning the additional items of the narrowed-down image data. Note that the image list generated by the image list generation unit 253 may have a table form like image lists L1 and L2 shown in FIG. 2 or a thumbnail form like an image list LS shown in FIG. 3. In addition, in this case, upon accepting the input of a list display request from the input device 150, the image list generation unit 253 generates an image list corresponding to the display areas designated by the list display request. However, for example, the image list generation unit 253 may generate an image list without accepting the input of a list display request. In this case, the image list generation unit 253 needs to generate image lists respectively corresponding to all the display areas after the image acquisition unit 252 acquires image data.

The image list display unit 254 displays the image lists generated by the image list generation unit 253 in display areas on the monitor 200. Note that the image list display unit 254 may display the image lists in the display areas corresponding to the image lists, as shown in, for example, FIG. 4, or may display the image lists in arbitrary display areas of the display areas on the monitor 200 (that is, may display the image lists over a plurality of display areas of the display areas on the monitor 200). In addition, the image list display unit 254 can enlarge/reduce the image list displayed on the monitor 200 by accepting a predetermined input (for example, double clicking with the mouse) from the input device 150.

Upon accepting an input for the selection of image data in the image list displayed on the monitor 200, the selected image display unit 255 displays the selected image data in a corresponding display area on the monitor 200.

Figure 5:
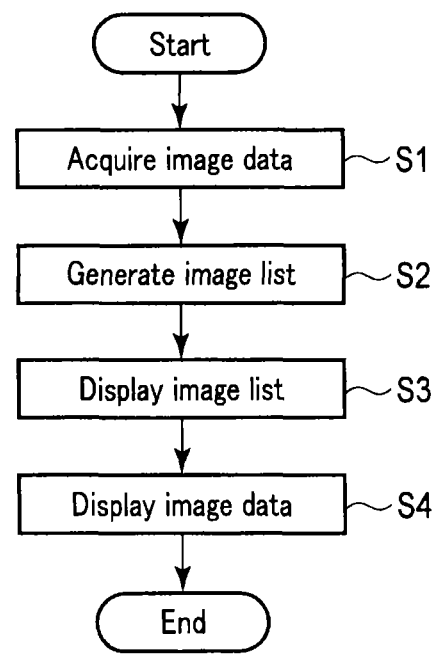
FIG. 5 is a flowchart showing an example of the operation of the image observation apparatus according to this embodiment.

An example of the operation of the image observation apparatus 250 having the above arrangement will be described next with reference to the schematic views of FIGS. 2 and 4 and the flowchart of FIG. 5. Assume that in this case, the display image definition unit 251 has defined, in advance, display target conditions for deciding image data as display targets in the respective display areas, as shown in FIG. 2. Assume also that the display area A is designated by the list display request input from the input device 150.

Upon accepting the input of the patient ID input by the input device 150, the image acquisition unit 252 acquires image data containing the accepted input patient ID in additional information from the image data storage device 100 (step S1).

Subsequently, upon accepting the input of the list display request input from the input device 150, the image list generation unit 253 generates the image list L1 concerning the additional items of image data as a display target in the display area A designated by the accepted input list display request (step S2). In this case, since the modality ID of an X-ray CT angiographic apparatus is indicated as information to be contained in additional information added to the image data as the display target in the display area A, the image list generation unit 253 narrows down the image data acquired in step S1 to only image data containing the modality ID of the X-ray CT angiographic apparatus in additional information. Thereafter, the image list generation unit 253 generates the image list L1 like that shown in FIG. 2.

The image list display unit 254 then displays the image list L1 generated by the image list generation unit 253 in a display area on the monitor 200 (step S3).

Thereafter, upon accepting an input for the selection of one additional item in the image list L1 displayed by the image list display unit 254, the selected image display unit 255 displays image data corresponding to the selected additional item in the display area A, as shown in FIG. 4 (step S4).

The first embodiment described above can execute generation processing and display processing for an image list specialized for each display area with the arrangement including the display image definition unit 251 which defines display target conditions for deciding image data as a display target for each display area, the image list generation unit 253 which generates an image list after narrowing down acquired image data with the display target conditions defined by the display image definition unit 251, and the image list display unit 254 which displays the image list generated by the image list generation unit 253.

In addition, according to this embodiment, the image list display unit 254 can display an image list in a corresponding display area. Therefore, when selecting a desired additional item from a given image list, the operator can select an additional item corresponding to a desired image while referring to the additional items of the images already displayed in the remaining display areas.

[Second Embodiment]

Figure 6:
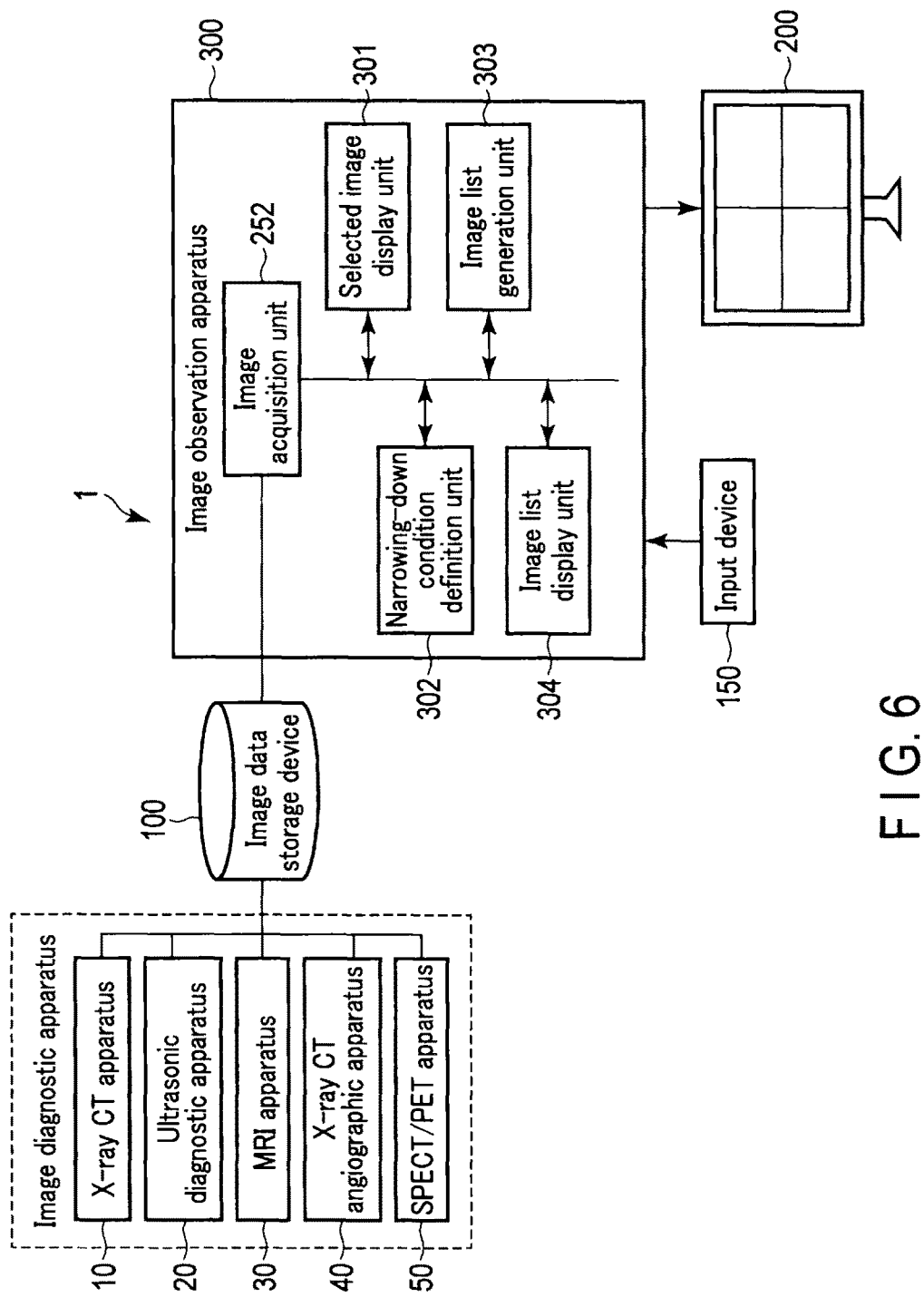
FIG. 6 is a schematic view showing an example of the arrangement of a medical image display system including an image observation apparatus according to the second embodiment.
Figure 7:
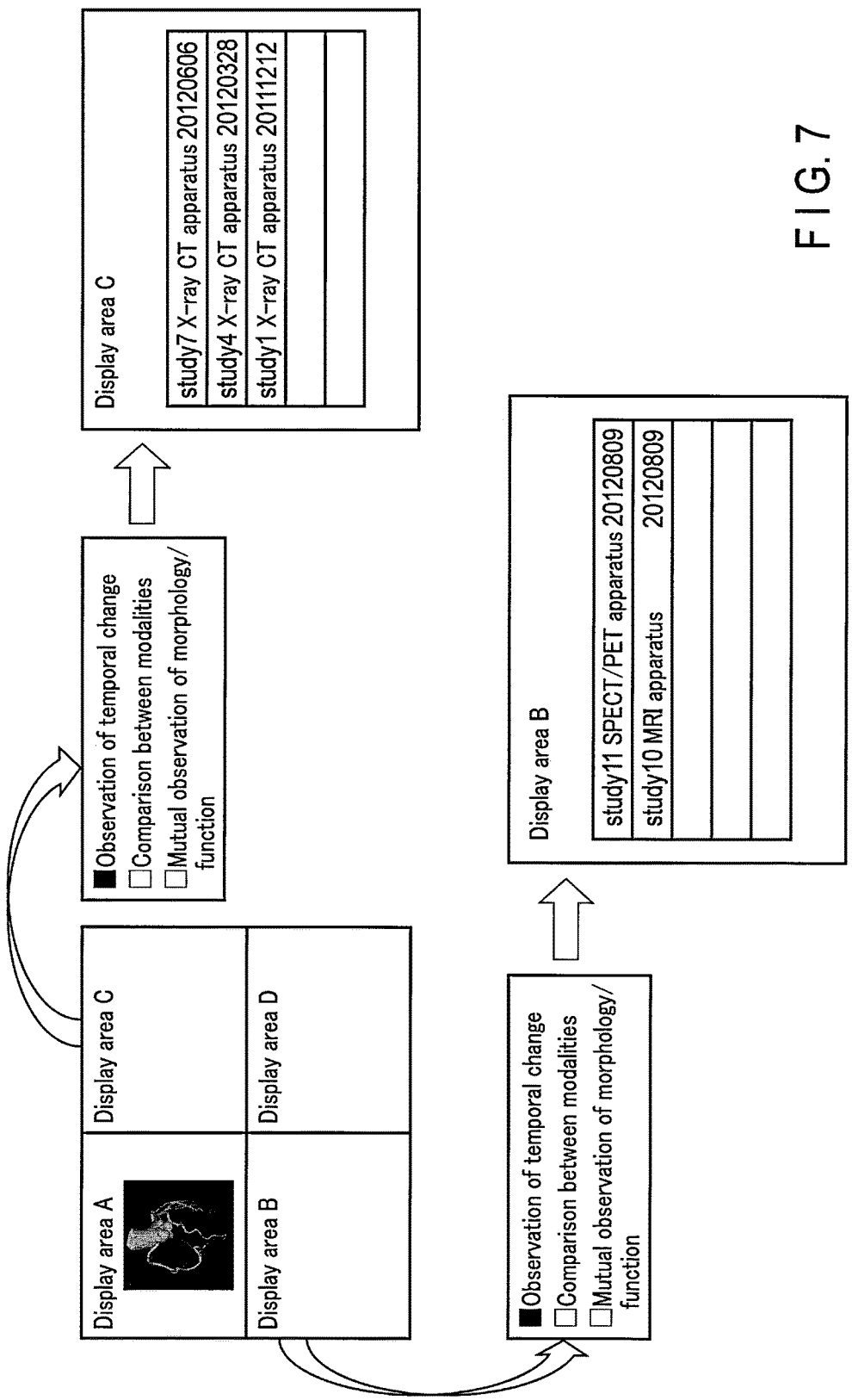
FIG. 7 is a schematic view showing an example of a process in which the image observation apparatus according to this embodiment displays an image list on a monitor.

FIG. 6 is a schematic view showing an example of the arrangement of a medical image display system including an image observation apparatus according to the second embodiment. The same reference numerals as in FIG. 1 denote functional units in FIG. 6 which have the same functions as in the first embodiment, and a detailed description of them will be omitted. FIG. 7 is a schematic view showing an example of a process in which the image observation apparatus according to this embodiment displays an image list on a monitor. Functional units having functions different from those in the first embodiment will be mainly described below.

As shown in FIG. 6, an image observation apparatus 300 includes an image acquisition unit 252, a selected image display unit 301, a display target condition definition unit 302, an image list generation unit 303, and an image list display unit 304. The image acquisition unit 252 has the same function as that in the first embodiment, and hence a detailed description of it will be omitted. The functions of the units 301 to 304 will be described below.

Upon accepting an input for the selection of one of the image data acquired by the image acquisition unit 252, the selected image display unit 301 displays the selected image data in the first display area as one of the display areas on a monitor 200. In addition, upon accepting an input for the selection of image data in the image list displayed by the image list generation unit 303, the selected image display unit 301 displays the selected image data in the second display area as one of the respective display areas on the monitor 200. If, however, image data in the image list displayed by the image list generation unit 303 is image data which can be combined with the image data displayed in the first display area, the selected image display unit 301 combines the image data displayed in the first display area with the selected image data and then displays the image data after the combining. Note that the operator can arbitrarily set, via an input device 150, which of the respective display areas on the monitor 200 are the first and second display areas. When the operator selects image data to be displayed in the first display area on the monitor 200, the first image list indicating a list of the additional items of all the image data acquired by the image acquisition unit 252 is displayed in a display area on the monitor 200.

The display target condition definition unit 302 defines display target conditions which are conditions for deciding image data as a display target in the second display area on the monitor 200, and which are formed from at least one additional item (excluding a patient ID) in additional information. More specifically, upon accepting the input of display target condition information input by the input device 150, the display target condition definition unit 302 defines display target conditions by writing the accepted input display target condition information in the memory (not shown). In this case, display target condition information is information which represents a condition defined by using at least one additional item in additional information to decide image data as a display target in the second display area on the monitor 200, and includes, for example, information (1) to information (6) to be described below. Note that the display target condition information stored in the memory (not shown) is information to which the image list generation unit 303 can refer to as needed.

The information (1) indicates that additional information contains an image ID different from that in the additional information of the image data displayed in another display area (e.g., the first display area).

The information (2) indicates that additional information contains a specific additional item, more specifically, a modality ID, in the additional information of the image data display in another display area.

The information (3) indicates that additional information contains a modality ID in the additional information of the image data displayed in another display area, and also contains imaging date information indicating a past study.

The information (4) indicates that additional information contains a modality ID different from that in the additional information of the image data displayed in another display area.

The information (5) indicates that additional information contains the type information of an image type different from the image type (i.e., a morphological image or functional image) indicated by type information in the additional information of the image data displayed in another display area.

The information (6) indicates that additional information contains the modality ID of an image diagnostic apparatus which captures image data which can be combined with the image data captured by an image diagnostic apparatus indicated by the modality ID in the additional information of the image data displayed in another display area, and also contains imaging region information in the additional information of the image data in the another display area.

Note that although this embodiment has exemplified the information (1) to the information (6) as condition information, condition information is not limited to them and can be arbitrarily set by the operator via the input device 150.

The image list generation unit 303 narrows down the image data acquired by the image acquisition unit 252 to only image data containing, in additional information, the same information as that of a specific additional item in the additional information of the image data displayed in the first display area by the selected image display unit 301 while referring to the display target condition information stored in the memory (not shown), and generates the second image list indicating a list concerning the specific additional item of the narrowed-down image data and other additional items. The image list generation unit 303 also generates an image list indicating a list of additional items of all the image data acquired by the image acquisition unit 252, i.e., the first image list indicating a list of additional items of image data as a display target in the first display area on the monitor 200. Note that if one piece of display target condition information is stored in the memory (not shown), the image list generation unit 303 generates the second image list while referring to the stored display target condition information. If a plurality of pieces of display target condition information are stored in the memory (not shown), the image list generation unit 303 generates the second image list while referring to the selected display target condition information after making the operator select which of the pieces of display target condition information is to be used, as shown in, for example, FIG. 7.

Note that in this embodiment, the image list generation unit 303 generates the second image list of image data as a display target in the second display area on the monitor 200. However, for example, the image list generation unit 303 can generate an image list of image data as a display target in the third display area as one of the respective display areas on the monitor 200. In this case, the image list generation unit 303 may narrow down the image data acquired by the image acquisition unit 252 to only image data containing information concerning information in the additional information of the image data displayed in the first display area in additional information, only image data containing information concerning information in the additional information of the image data displayed in the second display area in additional information, or only image data containing information concerning information in the additional information of the image data displayed in the first and second display areas in additional information.

The image list display unit 304 displays the first and second image lists generated by the image list generation unit 303 on display areas on the monitor 200. Note that the image list display unit 304 may display the first and second image lists on the first and second display areas respectively corresponding to the image lists, or may display the image lists on arbitrary display areas of the display areas on the monitor 200. In addition, the image list display unit 304 can enlarge/reduce the image list displayed on the monitor 200 by accepting a predetermined input (e.g., double clicking with the mouse) from the input device 150.

An example of the operation of the image observation apparatus 300 having the above arrangement will be described next with reference to the flowchart of FIG. 8. Assume that display target condition information is stored in a memory (not shown) in advance.

First of all, upon accepting the input of the patient ID input by the input device 150, the image acquisition unit 252 acquires image data containing the accepted input patient ID in additional information from an image data storage device 100 (step S11).

Subsequently, the image list generation unit 303 generates the first image list indicating a list of all the image data acquired by the image acquisition unit 252, and the image list display unit 304 displays the generated first image list on a display area on the monitor 200 (step S12).

Upon accepting an input for the selection of image data in the first image list displayed by the image list display unit 304, the selected image display unit 301 displays the selected image data in the first display area on the monitor 200 (step S13).

Subsequently, the image list generation unit 303 narrows down the image data acquired by the image acquisition unit 252 to only image data containing, in additional information, information concerning information in the additional information of the image data displayed in the first display area on the monitor 200 while referring to the display target condition information stored in the memory (not shown), and generates the second image list indicating a list of the additional items of the narrowed-down image data (step S14).

The image list display unit 304 then displays the second image list generated by the image list generation unit 303 in a display area on the monitor 200 (step S15).

Thereafter, upon accepting an input for the selection of image data in the second image list displayed by the image list display unit 304, the selected image display unit 301 displays the selected image data in the second display area on the monitor 200 (step S16).

The second embodiment described above can execute generation processing and display processing for an image list specialized for each display area with the arrangement including the display target condition definition unit 302 which defines display target conditions by using at least one piece of information in additional information to decide image data as a display target in the second display area, the image list generation unit 303 which generates the second image list by narrowing down the acquired image data to only image data containing, in additional information, information concerning information in the additional information of the image data displayed in the first display area in accordance with the display target conditions defined by the display target condition definition unit 302, and the image list display unit 304 which displays the second image list generated by the image list generation unit 303.

In addition, according to this embodiment, the image list display unit 304 can display the second image list in the second display area. Therefore, when selecting desired image data from the second image list, the operator can select the desired image while referring to the image data already displayed in the first display area.

At least one of the embodiments described above can provide an image observation apparatus and its storage medium which allow the operator to efficiently select desired image data with the arrangement configured to execute generation processing and display processing for an image list specialized for each display area on the monitor 200.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An image observation apparatus comprising:
a condition memory configured to store a plurality of display target conditions respectively corresponding to a plurality of display areas in a display screen;
processing circuitry configured to
extract additional information of a plurality of images displayed to the plurality of the display areas respectively, and
generate a plurality of image lists based on the extracted additional information, wherein each of images in the image list has corresponding additional items to the extracted additional items in response to a request to display the image lists, the image lists respectively corresponding to the plurality of display areas; and
a monitor configured to display an image list of the plurality of image lists in each of the plurality of display areas, and an image corresponding to an additional item selected from the plurality of displayed image lists in the corresponding display area.

2. The image observation apparatus according to claim 1, wherein the processing circuitry selects one of the plurality of display areas, selects, upon inputting of the request to display the image list in the selected display area, the plurality of images corresponding to display target conditions corresponding to the selected display area in response to the request, and generate the image list concerning the plurality of selected images.

3. The image observation apparatus according to claim 2, wherein the monitor displays the generated image list in the selected display area in accordance with the request.

4. The image observation apparatus according to claim 1, wherein the additional item includes at least one of a modality type, an image type, a study date, a modality ID, an imaging date, an imaging region, a functional image/morphological image type, an image acquisition condition, contrast agent information, a study order, a study ID, and a series ID.

5. The image observation apparatus according to claim 1, wherein the plurality of display target conditions include different modality types.

6. An image observation apparatus which is configured to access a memory storing data of a plurality of images with a patient ID identifying a patient and at least one of a modality type, an image type, an study date, a modality ID, an imaging date, an imaging region, a functional image/morphological image type, an image acquisition condition, contrast agent information, an study order, an study ID, and a series ID, and includes a plurality of image display areas, the image observation apparatus comprising:

an input device configured to input the patient ID;

a transmitter configured to transmit a request to provide an image, together with the input patient ID, to the memory;

processing circuitry configured to narrow down the plurality of images according to a first additional item accompanied in an image selected from the plurality of images in response to the request, the plurality of images are transmitted from the memory, and generate an image list including information concerning the first additional item by use of a second additional item accompanied in the narrowed-down image; and a monitor configured to display the selected image in a first display area as one of the plurality of image display areas, the generated image list, and an image corresponding to the second additional item selected from the displayed image list in the second display area as one of the plurality of image display areas.

7. The image observation apparatus according to claim 6, wherein the monitor displays the generated image list in the second display area.

8. The image observation apparatus according to claim 6, wherein the first additional item includes at least one of a modality type, an image type, and a study date.

9. The image observation apparatus according to claim 6, wherein the plurality of provided images are narrowed down to an image added with a modality type different from a modality type of the selected image and the same image type as that of the selected image.

10. A non-transitory computer-readable recording medium including computer executable instructions, wherein the instructions, when executed by a computer, cause the computer to perform a method, the method comprising:

storing a plurality of display target conditions respectively corresponding to a plurality of display areas in a display screen;

extracting additional information of a plurality of images displayed to the plurality of the display areas respectively;

generating a plurality of image lists based on the extracted additional information, wherein each of images in the image list has corresponding additional items to the extracted additional items in response to a request to display the image lists, the image lists respectively corresponding to the plurality of display areas; and displaying an image list of the plurality of image lists in each of the plurality of display areas and an image corresponding to an additional item selected from the plurality of displayed image lists in the corresponding display area.

11. A non-transitory computer-readable recording medium including computer executable instructions, wherein the instructions, when executed by a computer, in image observation which is configured to access a memory storing data of a plurality of images with a patient ID identifying a patient and at least one of a modality ID, an imaging date, an imaging region, and a functional image/morphological image type, causes the computer to perform a method, the method comprising:

inputting the patient ID;

transmitting a request to provide an image, together with the input patient ID, to the memory;

displaying an image selected from a plurality of images provided from the memory in response to the request in one of the plurality of image display areas;

narrowing down the plurality of provided images according to a first additional item accompanied in the selected image;

generating an image list including information concerning the first additional item by use of a second additional item of the narrowed-down image;

displaying the generated image list; and displaying an image corresponding to the second additional item selected from the displayed image list in a second display area as one of the plurality of image display areas.

* * * * *